(12) United States Patent
Sheldon et al.

(10) Patent No.: US 6,436,418 B1
(45) Date of Patent: Aug. 20, 2002

(54) ABSORBENT ARTICLE WITH SKIN TREATMENT MEANS

(75) Inventors: Donald A. Sheldon, Downingtown; Ruth Levy, Collegeville; Christopher Ferdock, Perkiomenville, all of PA (US)

(73) Assignee: Tyco Healthcare Retail Services AG (CH)

( * ) Notice: Subject to any disclaimer, the term of this patent is extended or adjusted under 35 U.S.C. 154(b) by 0 days.

(21) Appl. No.: 09/438,898

(22) Filed: Nov. 12, 1999

(51) Int. Cl.[7] .................. A01N 25/34; A61F 13/00; A61F 13/15; A61L 15/00; A61K 31/74
(52) U.S. Cl. ............... 424/402; 424/404; 424/443; 424/445; 424/446; 424/405; 604/360
(58) Field of Search .............. 604/367; 424/78.06, 424/402, 404, 443, 445, 405, 446, 447, 78.02, 78.05, 78.03

(56) References Cited

U.S. PATENT DOCUMENTS

| | | | | |
|---|---|---|---|---|
| 4,695,278 | A | 9/1987 | Lawson | 604/385 |
| 4,795,454 | A | 1/1989 | Dragoo | 604/385.2 |
| 5,525,346 | A | 6/1996 | Hartung et al. | 424/402 |
| 5,609,587 | A | * 3/1997 | Roe | 604/360 |
| 5,618,529 | A | * 4/1997 | Pichierri | 424/78.06 |
| 5,763,333 | A | 6/1998 | Suzuki et al. | 442/351 |
| 5,998,692 | A | * 12/1999 | Roe et al. | 604/367 |
| 5,998,695 | A | * 12/1999 | Roe et al. | 604/367 |

FOREIGN PATENT DOCUMENTS

| | | |
|---|---|---|
| DE | 41 36 540 A | 11/1991 |
| WO | WO 99 56796 | 11/1999 |
| WO | WO 99/56796 | * 11/1999 |

OTHER PUBLICATIONS

International Search Report of corresponding foreign Application No. PCT/US 00/30491.

* cited by examiner

Primary Examiner—Thurman K. Page
Assistant Examiner—Blessing Fubara
(74) Attorney, Agent, or Firm—Caesar, Rivise, Bernstein, Cohen & Pokotilow, Ltd.

(57) ABSTRACT

A disposable absorbent article, e.g., a diaper, feminine hygiene product, adult incontinent product, etc., arranged to be worn by a wearer to trap and collect fluid waste products, e.g., menses, feces and/or urine, of the wearer. The article has a flexible chassis and plural tabs for holding the diaper in place on the wearer. The chassis is made up of a top-sheet, a fluid absorbent core and a skin-treatment agent, e.g., zinc oxide, vitamins A, D and E, allentoin, aluminum hydroxide, Calamine, dimethicone, glycerin, kaolin, shark liver oil, cod liver oil, zinc acetate, lanolin, mineral oil, zinc carbonate, talc, titanium oxides, silver oxides, and combinations thereof. The top sheet is formed of a fluid pervious material, e.g., a fibrous material or a polymeric apertured three dimensional film. In one embodiment the agent(s) is(are) disposed on the surface of the top sheet which is located immediately adjacent the skin of the wearer when the article is in place, in another embodiment the agent(s) is(are) incorporated into the material making up the top sheet.

31 Claims, 2 Drawing Sheets

ABSORBENT ARTICLE WITH SKIN TREATMENT MEANS

FIELD OF THE INVENTION

This invention relates generally to disposable absorbent articles and more specifically to disposable absorbent articles, e.g., diapers, feminine hygiene products, adult incontinent products, etc., which include materials for treating the skin of the wearer to prevent and/or treat hydrated skin induced irritation(s), e.g., diaper rash.

BACKGROUND OF THE INVENTION

Disposable diapers typically include a liquid absorbent core located between a top-sheet and a back sheet. The top-sheet is commonly formed of a material which is pervious to body fluids, e.g., urine, to promote the transfer of such fluids into the core with minimal fluid retention by the top-sheet. The back-sheet is commonly formed of a liquid impervious or hydrophobic material to form a barrier wall so that any fluid absorbed by the article cannot escape out the back-sheet. In many cases, a fluid "acquisition," "surge" or "transfer" layer is located between the top-sheet and the core to facilitate the transference of body fluid(s) into the core.

The absorbent core of many disposable diapers and other higher performance incontinence products, e.g., adult briefs, typically have cores with enhanced absorbency capability. This enhanced absorbency can be accomplished by use of an air-laid super absorbent material, or by the inclusion of absorbency enhancers, e.g., materials sometimes referred to as "super-absorbent-polymers" (which may be in the form of particles or fibers) with other absorbent materials, such as a fluff, e.g., comminuted wood pulp or other cellulosic fibers. Examples of super absorbent materials are hydrogel polymer particulates, sometimes referred to as "SAP," and hydrogel polymer fibers, sometimes referred to as "SAF."

As will be appreciated feces and/or urine which contacts the skin of the wearer of the diaper can frequently result in the irritation of the skin, e.g., "diaper rash." Thus, the prevention or treatment of diaper rash or similar skin irritation is a considerable factor to be addressed by the personal care products industry. To that end various topical lotions or creams are available commercially to treat and/or prevent diaper rash. Among t he ingredients in such lotions are zinc oxide and vitamins A and D.

The patent literature also includes patents directed to lotions for the prevention or treatment of diaper rash. For example, In U.S. Pat. No. 5,618,529 (Pichierri) there is disclosed a diaper rash treatment in the form of a composition containing a copolymer of a lower alkyl vinyl ether and maleic acid or a derivative of the copolymer which is stated to constitute an improvement over prior art diaper rash treatments, such as zinc oxide, vitamins A, D and D3, or combinations thereof.

The patent literature also includes various patents directed to emollients or other skin conditioner or treatments which may be incorporated in diapers or other absorbent articles. For example, U.S. Pat. No. 5,525,346 (Hartung et al.) discloses a diaper including a diaper rash lotion or cream impregnated sheet. The lotion or cream of the sheet is an alleged improvement over zinc oxide formulated with an oily substance, such as petrolatum, since that type of zinc oxide diaper rash treatment is stated to be "greasy, messy to apply, and not easily removed from the hands or the baby's bottom."

In U.S. Pat. No. 5,763,333 (Suzuki et al.) there is disclosed a composite sheet absorbent article, e.g., a diaper. The composite sheet includes a moisture permeable porous sheet formulated by compounding a polyolefin resin with a filler. Various inorganic fillers are disclosed, namely, calcium carbonate, gypsum, talc, carbon black, clay, kaolin, silica, diatomaceous earth, magnesium carbonate, barium carbonate, magnesium sulfate, barium sulfate, calcium sulphate, calcium phosphate, aluminum hydroxide, zinc oxide, magnesium oxide, titanium oxide, alumina, mica, asbestos powder, sirasu balloon, zeolite, terral alba, cement, silica fume, and mica powder. Various organic fillers are also disclosed, namely, woodmeal coal powder, and pulp powder.

U.S. Pat. No. 5,609,587 (Roe) discloses a diaper having a top sheet including a lotion in the form of a liquid polyol polyester emollient and an immobilizing agent. The lotion compositions are also disclosed as optionally comprising water, pH reducing or buffering systems, vitamins, skin soothing agents or anti-inflammatories, viscosity modifiers, perfumes, disinfectant antibacterial actives, pharmaceutical actives, film formers, deodorants, opacifiers, astringents, solvents and the like. Suitable vitamins disclosed are vitamins A and E. Suitable skin soothing agent or anti-inflammatories disclosed include aloe vera and panthenol.

Notwithstanding the above prior art, a need presently exists for a diaper or other disposable absorbent article which deters the formation and/or lessens the effects of diaper rash or other skin irritation.

OBJECTS OF THE INVENTION

It is a general object of this invention to provide a disposable absorbent articles, e.g., diapers, feminine hygiene products, adult incontinent products, etc., which address the needs of the prior art.

It is a further object of this invention to provide disposable absorbent articles, e.g., diapers, feminine hygiene products, adult incontinent products, etc., which include a treatment agent arranged to engage the skin of the wearer of the article to deter the formation and/or lessen the effect of skin irritation.

SUMMARY OF THE INVENTION

A disposable absorbent article, e.g., a diaper, which is arranged to be worn by a person to trap and collect fluid waste products, e.g., feces and urine.

The absorbent article basically comprises a top-sheet, an absorbent core and a skin-treatment agent. The top-sheet is formed of a liquid pervious, e.g., hydrophilic, material. The skin-treatment agent, e.g., zinc oxide, vitamins A, D and E, allentoin, aluminum hydroxide, Calamine, dimethicone, glycerin, kaolin, shark liver oil, cod liver oil, zinc acetate, lanolin, mineral oil, zinc carbonate, talc, titanium oxides, silver oxides, and combinations thereof, is incorporated into the article in such a manner that it will contact portions of the skin of the wearer which would be susceptible irritation by the fluid waste products to deter such irritation or to lessen the effect thereof.

DETAILED DESCRIPTION OF THE PREFERRED EMBODIMENT

Figure 1:
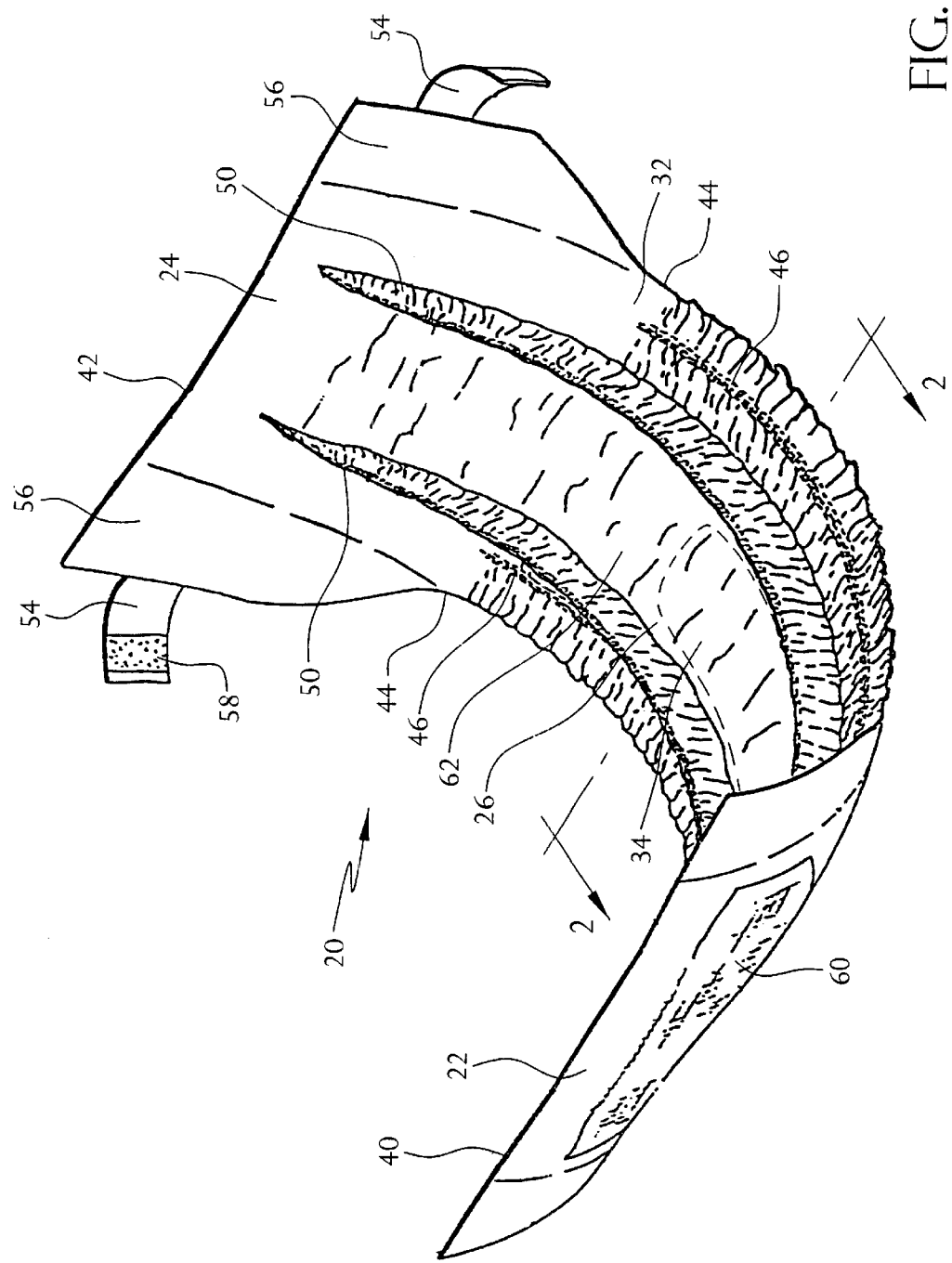
FIG. 1 is an isometric view of one preferred embodiment of the subject invention, e.g., a diaper.

Referring now to the various figures of the drawing wherein like reference characters refer to like parts, there is shown in FIG. 1 a disposable absorbent article 20 constructed in accordance with one embodiment of this invention. It should be pointed out that as used herein the term "disposable" means that article is designed to be used until soiled, either by urination or otherwise, and then discarded, rather than being washed and used again.

In the embodiment of FIG. 1 the article 20 is in the form of a diaper. While the following description will focus on diapers, it should be clear that the subject invention can be used for any type of absorbent article or garment to be worn by a person for trapping menses, feces and/or urine.

Figure 2:
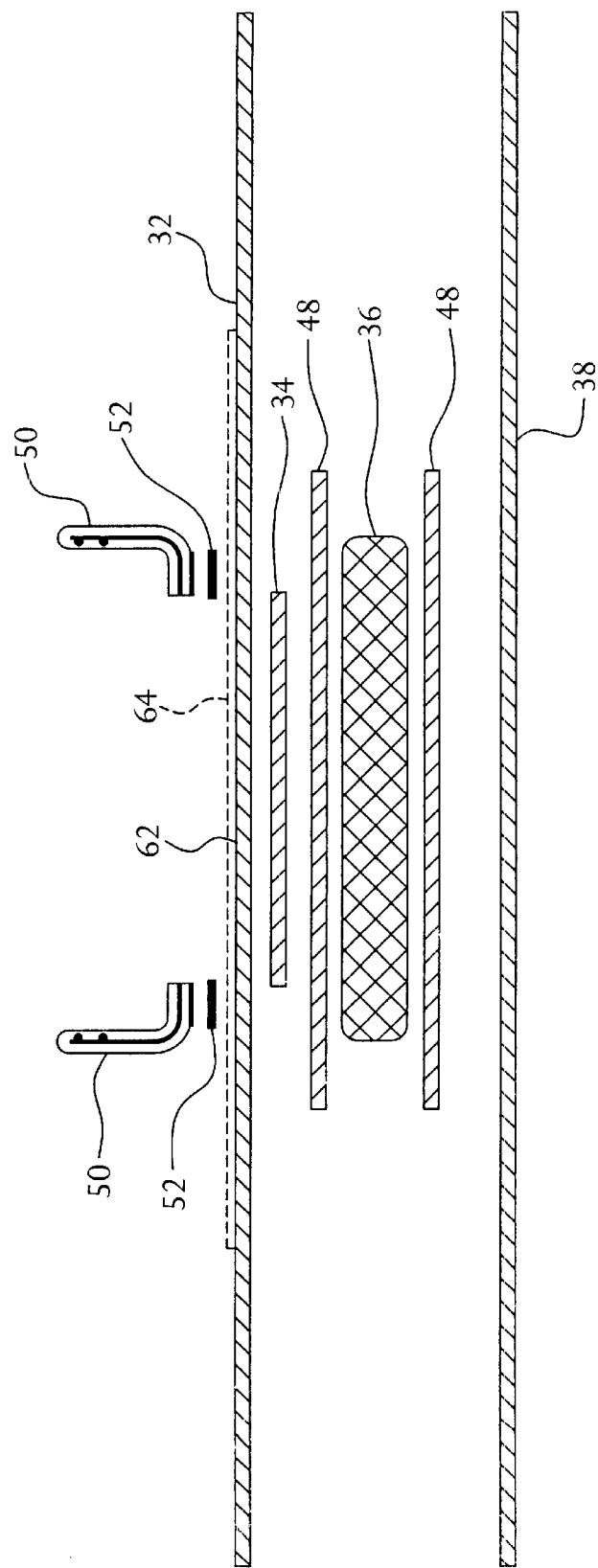
FIG. 2 is an enlarged, exploded sectional view taken along line 2—2 of FIG. 1.

The diaper 20 basically comprises a chassis including a front waist portion 22, a back waist portion 24, and a crotch portion 26 and is of generally conventional construction, except for the inclusion of one or more skin-treatment agents therein. Prior to describing those agents a brief description of the other portions of the diaper will now be discussed. To that end and as best seen in FIG. 2, the diaper 20 basically comprises a body-side liner or top-sheet 32, a fluid acquisition system 34, a liquid absorbent structure or core 36, and an outer cover or back-sheet 38.

The top-sheet 32 is arranged to face toward the body of the user, when the diaper is in place, with the back-sheet facing away from the wearer. The top-sheet is superimposed over the back-sheet, with the absorbent core 36 interposed therebetween. The fluid-acquisition system 34 is located on top of the core and under the top-sheet to facilitate the passage of liquid waste into the core for absorption thereby. The top-sheet 32 and/or back-sheet 38 can be any suitable shape and dimensions for other designs or constructions, as will be clear from the other embodiments disclosed herein.

The back-sheet 38 comprises front edge 40, a back edge 42, and a pair of side edges 44. Each side edge includes a central, cut-out to define a respective leg cut out. The crotch portion 26 of the diaper is located between the leg cut-outs.

The top-sheet 32 may be of the same shape as the back-sheet 38 or of a different shape and is bonded to the back-sheet 38 around its entire periphery, with the absorbent material core 36 and the fluid acquisition system 34 interposed therebetween. The back-sheet and top-sheet can be joined together in any suitable manner, e.g, by adhesive bonding. The adhesives can be applied in any manner such as by spraying, slot-coat extrusion, printing, or the like. The applied adhesive can be in any desired configuration or design, such as continuous or discontinuous beads, continuous or discontinuous swirls, meltblown patterns, spray patterns, or the like. Alternatively, the joining of layers and structures can be accomplished by heat sealing, ultrasonic bonding, or the like.

Each lateral side edge 44 of the diaper 20 is elasticized by means of plural, e.g., three, longitudinally extending elastic, e.g., LYCRA 940 decitex, threads or strands 46 disposed along the length of the cut away portion of that side edge. The strands may be attained from E. I. DuPont de Nemours and Company, Wilmington, Del., and are held in place by a suitable elastic adhesive, such as that used to hold the elastic foam of the waist portion in place. The elastic adhesive is intermittently applied along the top sheet to allow the diaper to be actively stretchable along the leg cut outs and not all the way to the edges of the respective waist portions, thereby enable the diaper to closely conform about the legs of the wearer for impeding the egress of waste material from the crotch region, as is conventional. Other arrangements can be used to elasticize the sides of the crotch portion of the diaper. For example, in lieu of plural longitudinally extending elastic threads 46, multiple strands of elastic material can be arranged in other orientations, intersecting, diagonal, or any combination thereof, or can be a film or laminate of various types of elastomeric material.

The back-sheet 38 or cover is preferably formed of a laminated sheet of a non-woven material and film (with the non-woven side positioned as the outermost layer). Such material should be hydrophobic, soft in texture, and strong in tensile strength. One particularly suitable material is a spunbond-meltblown-spunbond (SMS) web having a basis weight of about 15 gms per square meter (gsm), available from AVGOL Nonwoven Industries LTD., Holon, Israel. The spunbond layer is made of polypropylene fibers. Such composites provide the dual advantages of liquid barrier properties of film along with a soft, warm outer fabric texture. The non-woven outer cover can also be made of other suitable cloth-like materials, e.g., spun-bond or thermal-bond non-woven web made of either polypropylene, polyethylene, polyester, bi-component fibers (polyethylene/polypropylene or polyethylene/polyester), or any combinations of these fibers. Various multiple layer configurations or fiber denier variations may be used. Another example includes hydro-entangled non-woven webs, which may contain some cotton and/or rayon fibers blending in with thermal-plastic fibers. Cellulose fibers can also be blended in at small percentages to reduce cost. Still another example is a non-woven outer-cover made of stretchable or elastic materials, such as elastomeric composites of non-woven(s) and elastic membranes or a single layer of elastic material. The elastomeric composite can comprise of an inner layer of pre-stretched extruded elastic film sandwiched between and attached to a pair of non-woven webs. The non-woven webs may consist of spun-bond web, thermal-bond web, or a combination of the two. Preferably, the elastic film is made of synthetic rubber and the non-woven made of spun-bond polypropylene.

Other materials for forming the back-sheet 38 may include polypropylene films, co-extruded films (polyethylene and ethylene vinyl acetate), co-polymer films (polyethylene/polypropylene), and polylaminates (polypropylene nonwoven and polyethylene film). Still another example is a film made of a "breathable" microporous polyethylene. Suitable breathable films are available from Exxon Chemical Company, Buffalo Grove, Ill. This material allows water vapor to pass through it over time, while being impervious to liquid water. The water vapor transmission rate may range from 200–3000 grams per square meter per 24-hour period.

The fluid-acquisition system 34 is constructed to manage, transport, accommodate and/or direct high volumes and high flow rates of urine or other body fluid received from the top sheet target zone into the absorbent core 36 at a rate that the core can handle, despite multiple insults of such fluid.

In order to enable urine to quickly and efficiently pass through the top-sheet and into the underlying acquisition system 34 for subsequent transference to the absorbent core 36 for trapping therein, the top-sheet 32 is preferably liquid permeable. In particular, the top sheet may be selected from a variety of textile-like films and fabrics. Suitable fabrics include non-woven materials that are pervious to liquid, soft and pliable. Preferred nonwoven materials include spunbonded polypropylene; spunbonded polyethylene; thermally bonded webs of staple fibers preferably polypropylene or sheath/core bi-component fibers having a core of polyester or polypropylene and a sheath of polyethylene. To enhance the fluid control properties of the aforementioned liners, surfactants or wetting agents typified by Triton X-100 and Triton X-102 available from Rohm & Haas Company of Philadelphia, Pa. may be applied to the fluid receiving zones of the liner selectively having the outer zones untreated to reduce migration excreted fluid such as urine into the outer diaper regions leading to diaper leakage.

If desired, the top sheet 32 may be formed of a liquid impermeable material having plural apertures or pores extending therethrough so as to make the material liquid permeable.

The absorbent core 36 is a rectangular member which is centered in the diaper and extends from close to the front waist edge to close to the back waist edge. The core can be made up of any suitable absorbent material, as well as combinations of different types of absorbent material(s). For example, in the preferred embodiment of FIG. 1 the absorbent core 36 is formed of a mixture of pulp fluff and SAP wrapped in a liquid permeable tissue wrap 48 (only two sheets of which are shown in FIG. 2). Examples of SAP include polyacrylamides, polyvinyl alcohol, polyacrylates, various grafted starches, and the like. A desired super absorbent material is a cross-linked polysodium acrylate, which can be purchased from Chemdal Corporation, Palatine, Ill., under the trademark ASAP. The super absorbent materials can be in various geometric forms, such as various shaped particles, fibers, foams, and layers. The fluff and SAP are present in a ratio of about 10.5 grams SAP and 16.5 grams fluff, for a size 4 diaper, and have a core density range of about 0.18 to 0.22 grams per cubic centimeter.

Moreover, the core 36 can be of any shape and can be a single, integral absorbent structure, or can comprise a plurality of individual separate absorbent structures and/or absorbent materials that are operably assembled together. It can also consist of air-laid non-woven web that contains super-absorbent particles and/or super-absorbent fibers, polymeric binder and cellulose pulp fibers. In one exemplary embodiment the absorbent core is sandwiched between two plies of tissue, is aligned on top of the back-sheet and adhered down with construction adhesive. The tissue has a basis weight of 17.1 gsm. Suitable tissues are available from Cellu Tissue Corporation, East Hartford, Conn. The absorbent core is centered along the transverse direction and registered in the machine (longitudinal) direction within the diaper's chassis.

The amount of each absorbent material and SAP/fluff ratio depends on the size of the brief, e.g., "Small", "Medium", "Large" or "Extra Large" and the construction of the liquid acquisition or transfer system 34.

The diaper 20 also includes a pair of conventional "standing leg gathers" or cuffs 50 or liquid-impervious gaskets to provide leakage control in the crotch region. The standing leg gathers are located so that they extend along the leg opening region of the diaper as disclosed in U.S. Pat. No. 4,695,278 (Lawson) and U.S. Pat. No. 4,795,454 (Dragoo), both of which are incorporated by reference herein. Each standing leg gather is elasticized and extends from the edge of the front waist portion to the edge of the rear waist portion and along a respective side marginal edges of the core 36 and upstanding from the top-sheet 32. The standing leg gathers are secured in place by a suitable adhesive, e.g., construction adhesive 52.

The diaper 20 is arranged to be held in place on the body of the wearer in a conventional manner, e.g., by means of a pair of fastening tabs or tapes 54 projecting outward from a pair of respective ear portions 56 forming the side edges of top sheet 32 of the diaper contiguous with its back waist portion 42. In particular, each tab 54 includes a patch 58 of a myriad of small hooks on its underside surface. Each patch is arranged to be releasably secured to a "landing zone" portion 60 on the outer cover in the front waist region of the diaper. The landing zone is located at a position so that when the diaper is folded in half with the front waist portion disposed opposite the back waist portion, the landing zone 60 will be aligned with the tabs 54.

The landing zone 60 basically comprises a rectangular panel of whose outer surface comprises a myriad of small loops arranged to be engaged by the small hooks of the patch 58 of each fastening tab.

When the diaper is in place on the person with the front waist portion disposed over the lower abdomen, the back waist portion disposed over the lower back and buttocks region, and the crotch portion between the legs, each tab 54 may be brought into engagement with the a portion of the landing zone 60 closest to that tab on the front portion of the diaper so that the myriad of hooks on the patch engage the myriad of loops of the landing zone 60 to releasably secure the tab thereto. Any suitable multi-hook and multi-loop materials may be used. Particularly suitable multi-hook patches 54 are available from YKK (U.S.A.), Inc., Marietta, Ga., under the model designation Microhook (D-7) or Macrohook (EL "B"), while particularly a suitable multiloop material is a polyester fiber material having a basis weight of 1.55 ounce per square yard with a laminated polypropylene film (8 mil.) backing is available from FAB Industries, Inc, New York, N.Y.

Alternatively the tabs 54 may be in the form of adhesive tapes, such as those available from 3M Corporation, St. Paul, Minn., and the landing zone may be formed of a polyester film with a pre-applied adhesive in a selected print pattern, such as also available from 3M Corporation, St. Paul, Minn.

If desired the core 36 may be held in place by a hydrophillic construction adhesive, such as Cycloflex from National Starch and Chemical Corporation, Bridgewater, N.J.

The most preferred embodiments of skin treatment agents contemplated by this invention are zinc oxide and vitamins A and D, but other agents, such as allentoin, aluminum hydroxide, Calamine, dimethicone, glycerin, kaolin, shark liver oil, cod liver oil, zinc acetate, lanolin, mineral oil, zinc carbonate, talc, titanium oxides and silver oxides, can be used as well.

With respect to those articles making use of zinc oxide as the skin-treatment agent, the zinc oxide can either be incorporated into the material forming the top sheet 32 or can be applied on the exposed surface 62 of the top sheet 32 which will be disposed immediately adjacent the skin of the wearer when the diaper is in place. With respect to the former, zinc oxide particles can be melted in with the polymer making up the top sheet 32 so that when the polymer is extruded into a fiber form (for a fibrous top sheet) or into a thin sheet or film (for an apertured film top sheet) the molecules of the polymer, e.g., propylene or similar polymers, crystallize to thereby physically move the zinc oxide to the surface of the fiber or film disproportionately to the interior of the fiber or film. Thus, there will be a substantial amount of the zinc oxide which has "bloomed out" onto the surface 62 of fiber or film making up the top sheet 32 for engagement with the skin of the wearer.

The incorporation of zinc oxide into the polymeric material making up the top sheet fibers or film is contemplated as follows. Zinc oxide powder is introduced into a diluted, e.g., 10%–50% zinc oxide and 50%–90% polymer. Then the diluted compounded polymer is melted into the polymer for making up the fiber or film of the top sheet. If the polymer is to be made into fibers for a fibrous top sheet, it is contemplated to heat the polymer with the skin-treating agent therein to temperatures that are much higher than for use in making film, e.g., 400 to 600 degrees Fahrenheit. Then the polymer with the zinc oxide therein is extruded under high pressure through a tiny hole to form the fiber and to attenuate it. The fiber is then pulled on, either mechanically or with air, to help align all the molecules in the polymer. The zinc oxide particles being within the polymer tend to act as a "contaminant" so that they tend to move away from where the molecules of the polymer are forming chains within the fiber. Accordingly, the zinc oxide particles tend to "bloom" out of the fibers. This blooming action continues to occur over time so more of the zinc oxide particles become exposed through the surface of the fibers and while other zinc oxide particles remain mechanically entrapped within a portion of the fibers to keep them from falling off. Since the formation of polymeric film also entails some attenuation (albeit less than in the formation of polymeric fibers) when the polymer is melted and forced out of a slot form a very thin sheet, zinc oxide particles can be also be incorporated into polymeric film to bloom out.

While it is contemplated that all of the skin-treatment agents disclosed herein may be incorporated into the polymeric material making up the top sheet of the diaper, zinc oxide appears to be a particularly suitable candidate for incorporation.

Alternatively, the zinc oxide may be applied on the surface of the fibers used to make up a fibrous top sheet 32 or on the outer surface of an apertured film top sheet 32. In particular, the zinc oxide may be applied to the top sheet 32 with some type of immobilizing agent, e.g., petrolatum or petroleum jelly, or some other ointment, if the zinc oxide is in a form that is non-adhering, e.g., is a powder. The zinc oxide can also be applied by use of some type of diluting agent to form a suspension that will help attach it to the fiber/film of the top sheet by means of the surface tension of the suspension to the fiber/film. In particular, surfactants and/or alcohols and the like can be used to dilute the skin-treating agent. The diluted agent can then be applied to the surface of the fiber or film making up the top sheet and then dried to adhere the skin-treating agent to the fiber or film. In FIG. 2 the zinc oxide is shown on the surface of the top sheet by means of phantom lines designated by the reference number 64.

With respect to those articles making use of vitamins A and D as the skin-treatment agent, those vitamins can be in the form of cod liver oil (vitamins A and D are key components of cod liver oil) or shark liver oil, or in the purified chemical form. As is known cod liver oil is relatively thick. Thus, it may be applied directly to the top sheet 32 of the diaper like shown by the reference number 64 in FIG. 2. If desired, the cod liver oil may be used in a diluted form, e.g., a 5%–10% solution, applied onto the outer surface of the top sheet 32 of the diaper.

Vitamin A is an oil based compound, while vitamin D is a water based compound. Thus, if those vitamins are not used in the form of Cod Liver Oil, they can be applied to the top sheet of the diaper via a surfactant solution. In fact, even if those vitamins are in the form of Cod Liver Oil they can be applied to the top sheet with the surfactant.

It is also contemplated that vitamins A and D skin-treatment agent can be incorporated into the material forming the top sheet 32. The incorporation of the vitamins A and D into the fiber or film making up the top sheet is as follows:

A solution of vitamins A and D in purified form is introduced into the polymer pellet batch, then the polymer vitamin mixture is melted and extruded into fiber or sheet form. The fiber is then pulled on, either mechanically or with air, to help align all the molecules in the polymer. The vitamins A and D being within the polymer tend to act as a "contaminant" so that they tend to move away from where the molecules of the polymer are forming chains within the fiber. Accordingly, the vitamins A and D tend to "bloom" out of the fibers. This blooming action continues to occur over time so more of the vitamins A and D become exposed through the surface of the fibers and while some of the vitamins A and D remains mechanically entrapped within a portion of the fibers to keep them from falling off. Since the formation of polymeric film also entails some attenuation (albeit less than in the formation of polymeric fibers) when the polymer is melted and forced out of a slot form a very thin sheet, vitamins A and D can be also be incorporated into polymeric film to bloom out.

Irrespective of the composition of the skin-treatment agent(s) or the manner in which the skin-treatment agent(s) is(are) incorporated into the diaper, it(they) will be exposed from the exposed surface of the top sheet to engage the skin of the wearer, thus providing an irritation-inhibiting-action to either prevent or reduce waste-fluid-induced skin irritation. Moreover, if the skin treatment agent(s) is(are) incorporated in the diaper in the form of a lotion, cream or ointment which is suitable for transference from the portion of the diaper in which it is located to the skin of the wearer it can also serve to prevent the adhesion of feces and/or urine onto the skin. As will be appreciated the adherence of the skin-treatment agent(s) to the exposed skin should act to further reduce the likelihood of waste-induced irritation, e.g., diaper rash.

It should be pointed out that the exemplary embodiment of this invention, i.e., a diaper including the treatment agent, is just that, namely one example of various types of products which can incorporate the treatment agent. Thus, the subject invention can be used for products other than diapers, such as absorbent feminine hygiene products (e.g., sanitary napkins, panty liners, etc.), absorbent adult incontinent products (e.g., adult diapers, absorbent pads, shields, guards, under-pads, etc.). In fact, the subject invention has utility for any application wherein an absorbent product is in contact with hydrated skin which is therefor sensitive to irritation, e.g., diaper rash.

Moreover, it should be noted that the treatment agent(s) can be located on or incorporated into any portion of the absorbent article. For example, where the absorbent article is a diaper having standing leg cuffs or gathers, the treatment agent(s) can be located on or incorporated into such cuffs or gathers.

Without further elaboration the foregoing will so fully illustrate our invention that others may, by applying current or future knowledge, adopt the same for use under various conditions of service.

We claim:

1. A disposable adsorbent article arranged to be worn by the wearer to trap and collect fluid waste products of the wearer, said article comprising a top-sheet, a fluid absorbent core, and a skin-treatment agent, said top-sheet being formed of a liquid pervious material comprising fibers, said fibers comprising, an extrudate, said extrudate comprising a polymer and said skin treatment agent, whereupon said skin treatment agent can contact portions of the skin of the wearer which would be susceptible to irritation by the fluid waste products to deter such irritation or to lessen the effect thereof.

2. The disposable absorbent article of claim 1 wherein said skin-treatment agent comprises zinc oxide.

3. The disposable absorbent article of claim 1 wherein said skin-treatment agent comprises Vitamins A and D.

4. The disposable absorbent article of claim 1 wherein said skin-treatment agent is selected from the group consisting of zinc oxide, vitamins A, D and E, allentoin, aluminum hydroxide, Calamine, dimethicone, glycerin, kaolin, shark liver oil, cod liver oil, zinc acetate, lanolin, mineral oil, zinc carbonate, talc, titanium oxides, silver oxides, and combinations thereof.

5. The disposable absorbent article of claim 1 wherein said fibers form a non-woven web.

6. The disposable absorbent article of claim 5 wherein said fibers are selected from the group consisting of polypropylene, polyester, polyethylene, nylon, rayon, cotton, and blends and/or bicomponent fibers thereof.

7. The disposable absorbent article of claim 6 wherein said fibers are selected from the group consisting of through-air-bonded staple fibers, adhesively-bonded staple fibers, and thermally-point-bonded staple fibers.

8. The disposable absorbent article of claim 7 wherein said skin-treatment agent is selected from the group consisting of zinc oxide, vitamins A, D and E, allentoin, aluminum hydroxide, Calamine, dimethicone, glycerin, kaolin, shark liver oil, cod liver oil, zinc acetate, lanolin, mineral oil, zinc carbonate, talc, titanium oxides, silver oxides, and combinations thereof.

9. The disposable absorbent article of claim 1 wherein said top sheet is formed of a polymeric film.

10. The disposable absorbent article of claim 9 wherein said film is apertured.

11. The disposable absorbent article of claim 10 wherein said apertured film is three dimensional.

12. The disposable absorbent article of claim 11 wherein said skin-treatment agent is selected from the group consisting of zinc oxide, vitamins A, D and E, allentoin, aluminum hydroxide, Calamine, dimethicone, glycerin, kaolin, shark liver oil, cod liver oil, zinc acetate, lanolin, mineral oil, zinc carbonate, talc, titanium oxides, silver oxides, and combinations thereof.

13. The disposable absorbent article of claim 1 wherein said disposable absorbent article is a diaper.

14. The disposable absorbent article of claim 1 further comprising cuffs or gathers.

15. The disposable absorbent article of claim 14 wherein said cuffs or gathers are arranged to be disposed immediately adjacent the skin of the wearer when said article is in place, and wherein said skin-treatment agent is incorporated into said cuffs or gathers.

16. The disposable absorbent article of claim 15 wherein said skin-treatment agent is selected from the group consisting of zinc oxide, vitamins A, D and E, allentoin, aluminum hydroxide, Calamine, dimethicone, glycerin, kaolin, shark liver oil, cod liver oil, zinc acetate, lanolin, mineral oil, zinc carbonate, talc, titanium oxides, silver oxides, and combinations thereof.

17. A disposable absorbent article comprising cuffs or gathers arranged to be disposed immediately adjacent the skin of the wearer when said article is in place, and a skin-treatment agent incorporated into said cuffs or gathers.

18. The disposable absorbent article of claim 17 wherein said skin-treatment agent is selected from the group consisting of zinc oxide, vitamins A, D and E, allentoin, aluminum hydroxide, Calamine, dimethicone, glycerin, kaolin, shark liver oil, cod liver oil, zinc acetate, lanolin, mineral oil, zinc carbonate, talc, titanium oxides, silver oxides, and combinations thereof.

19. A process of making a disposable absorbent article comprising the steps of:
    combining a skin treatment agent with a polymer;
    heating said polymer and skin treatment agent combination;
    extruding said combination under high pressure though at least one tiny hole to provide plural fibers, wherein said fibers are used to form a top sheet of said disposable absorbent article;
    attenuating said fibers; and
    pulling said fibers to align molecules in said polymer.

20. The process of claim 19 further comprising the step of crystallizing said fibers to physically move said skin treatment agent to the surface of said fibers.

21. The process of claim 19 wherein said polymer is selected from the group consisting of propylenes.

22. The process of claim 19 wherein said disposable absorbent article is a diaper.

23. The process of claim 19 wherein said skin treatment agent is selected from the group consisting of zinc oxide, vitamins A, D and E, allentoin, aluminum hydroxide, Calamine, dimethicone, glycerin, kaolin, shark liver oil, cod liver oil, zinc acetate, lanolin, mineral oil, zinc carbonate, talc, titanium oxides, silver oxides, and combinations thereof.

24. A disposable adsorbent article arranged to be worn by the wearer to trap and collect fluid waste products of the wearer, said article comprising a top-sheet, a fluid absorbent core, and a skin-treatment agent, said top-sheet being formed of a liquid pervious material comprising fibers, said fibers comprising a polymer having very small bodies of said skin treatment agent which have bloomed to the outside of said fibers and very small bodies of said skin treatment agent within said fibers, whereupon said very small bodies of said skin treatment agent which have bloomed to the outside of said fibers can contact portions of the skin of the wearer which would be susceptible to irritation by the fluid waste products to deter such irritation or to lessen the effect thereof.

25. A disposable adsorbent article arranged to be worn by the wearer to trap and collect fluid waste products of the wearer, said article comprising a top-sheet, a fluid absorbent core, and a skin-treatment agent, said top-sheet being formed of a liquid pervious apertured film material comprising an extrudate of a polymer and said skin treatment agent, whereupon said skin treatment agent can contact portions of the skin of the wearer which would be susceptible to irritation by the fluid waste products to deter such irritation or to lessen the effect thereof.

26. A disposable adsorbent article arranged to be worn by the wearer to trap and collect fluid waste products of the wearer, said article comprising a top-sheet, a fluid absorbent core, and a skin-treatment agent, said top-sheet being formed of a liquid pervious apertured film material comprising a polymer having very small bodies of said skin treatment agent which have bloomed to the outside of said film and very small bodies of said skin treatment agent within said film, whereupon said very small bodies of said skin treatment agent which have bloomed to the outside of said film can contact portions of the skin of the wearer which would be susceptible to irritation by the fluid waste products to deter such irritation or to lessen the effect thereof.

27. A process of making a disposable absorbent article comprising the steps of:
    combining a skin treatment agent with a polymer;
    heating said polymer and skin treatment agent combination;

extruding said combination under high pressure though at least one very narrow aperture to provide a sheet, said sheet being used to form a top sheet of said disposable article; and forming a plurality of very small apertures in the film to make it fluid-pervious.

28. The process of claim 27 further comprising the step of crystallizing said sheet to physically move said skin treatment agent to the surface of said sheet.

29. The process of claim 27 wherein said polymer is selected from the group consisting of propylenes.

30. The process of claim 27 wherein said disposable absorbent article is a diaper.

31. The process of claim 27 wherein said skin treatment agent is selected from the group consisting of zinc oxide, vitamins A, D and E, allentoin, aluminum hydroxide, Calamine, dimethicone, glycerin, kaolin, shark liver oil, cod liver oil, zinc acetate, lanolin, mineral oil, zinc carbonate, talc, titanium oxides, silver oxides, and combinations thereof.

* * * * *